US00PP35825P2

(12) United States Plant Patent
Meilland

(10) Patent No.: US PP35,825 P2
(45) Date of Patent: May 28, 2024

(54) GROUND COVER ROSE PLANT NAMED 'MEIDEVI'

(50) Latin Name: *Rosa hybrida*
Varietal Denomination: MEIDEVI

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 161 days.

(21) Appl. No.: 18/086,949

(22) Filed: Dec. 22, 2022

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./104, 101, 103, 141, 145, 144, 117, Plt./118
CPC ... A01H 5/02; A01H 5/00; A01H 6/47; A01H 6/479
See application file for complete search history.

(56) References Cited

U.S. PATENT DOCUMENTS

PP6,384 P 11/1988 Meilland
PP8,362 P 9/1993 McGredy
PP28,054 P3 * 5/2017 Fonseca ..... Plt./103

OTHER PUBLICATIONS

Mobilian, Star Roses and Plants to showcase new varieties at Cultivate'22, Greenhous Management 2022, retrieved on Mar. 9, 2023 at https://www.greenhousemag.com/news/star-roses-and-plants-to-showcase-new-varieties-at-cultivate-22/, 14 pp. (Year: 2022).*
Star Roses and Plants for Buttercream Drift, retrieved on Mar. 9, 2023 at https://www.starrosesandplants.com/plants/buttercream-drift/, 4 pp. (Year: 2023).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of ground cover rose plant, referred to by its cultivar name, 'MEIDEVI', is disclosed. The new variety forms attractive, double cream colored flowers. Attractive semi-glossy foliage is formed, which contrasts beautifully with the blossoms. A ground cover growth habit is displayed. The new variety is well suited for providing attractive ornamentation in the landscape.

1 Drawing Sheet

Latin name of genus and species of plant claimed: *Rosa hybrida.*

Variety denomination: 'MEIDEVI'.

STATEMENT REGARDING PRIOR DISCLOSURES BY THE INVENTOR

The first offer for sale of the new variety was Mar. 4, 2022 in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented) from the cross between the 'MACIVY' variety (U.S. Plant Pat. No. 8,362) and the 'MEIGEKANU' variety (U.S. Plant Pat. No. 6,384). The male parent (i.e., the pollen parent) of the new variety was an unnamed seedling (not patented) from the cross between 'THE FAIRY' variety (not patented) and an unnamed seedling (not patented).

The parentage of the new variety can be summarized as follows:

('MACIVY'×'MEIGEKANU')×('THE FIARY'× Unnamed Seedling)

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms cream colored flowers,
(b) produces double flowers, and
(c) exhibits a ground cover habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent ('MACIVY'×'MEIGEKANU') displays orange colored flowers, whereas the new variety displays cream colored flowers. In addition, the unnamed pollen parent ('THE FAIRY'×Unnamed Seedling) produces white colored flowers, whereas the new variety produces cream colored flowers. Moreover, the new variety can be readily distinguished from other similar non-parental varieties. For example, the 'MEIZORLAND' variety (U.S. Plant Pat. No. 28,054) produces white colored flowers, whereas the new variety produces cream colored flowers.

The new variety has been named 'MEIDEVI'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately three years of age and were observed during July while budded on *Rosa laxa* and growing outdoors at Le Cannet des Maures, Var, France. Dimensions in centimeters are indicated at the bottom of the drawing.

Element 1—illustrates a specimen of a young shoot.
Element 2—illustrates a specimen of a floral bud before the opening of the sepals.
Element 3—illustrates a specimen of a floral bud at the opening of the sepals.
Element 4—illustrates a specimen of a floral bud at the opening of the petals.
Element 5—illustrates a specimen of a flower in the course of opening.
Element 6—illustrates a specimen of an open flower—plan view—obverse.
Element 7—illustrates a specimen of an open flower—plan view—reverse.
Element 8—illustrates a specimen of a fully open flower—plan view—obverse.
Element 9—illustrates a specimen of a fully open flower—plan view—reverse.
Element 10—illustrates a specimen of a flowering stem.
Element 11—illustrates a specimen of a floral receptacle showing arrangement of the stamens and pistils.
Element 12—illustrates a specimen of a floral receptacle showing arrangement of the pistils (stamens removed).
Element 13—illustrates a specimen of a leaf with 3 leaflets—plan view—upper surface.
Element 14—illustrates a specimen of a leaf with 3 leaflets—plan view—under surface.
Element 15—illustrates a specimen of a leaf with 5 leaflets—plan view—upper surface.
Element 16—illustrates a specimen of a leaf with 5 leaflets—plan view—under surface.
Element 17—illustrates a specimen of a leaf with 7 leaflets—plan view—upper surface.
Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of three-years-old specimens of the new variety during July while budded on *Rosa laxa* and growing outdoors at Le Cannet des Maures, Var, France.

Botantical classification: *Rosa hybrida* cultivar MEIDEVI.

Commercial classification: Ground Cover Rose Plant.

Plant:

*Habit.*—Ground cover.
*Height.*—Approximately 40 cm on average.
*Width.*—Approximately 60 cm on average.

Branches:

*Color.*—Young stems: commonly near Yellow-Green Group 146D. — adult wood: commonly near Yellow-Green Group 146B.
*Length.*—From the crown to the flower is typically between 15 cm to 30 cm.
*Diameter.*—Typically between 0.3 cm to 0.6 cm.
*Young shoots.*—Anthocyanin coloration: very slight.
*Thorns.*—Configuration on adult stems: concave, very elongated, and curved downwards on the upper surface and upright concave on the under surface. — long prickles — quantity: typically 1 thorn per 10 cm long young stem and typically 1 thorn per 10 cm long adult stem. — long prickles — length: approximately 0.7 cm on average on young stems and adult stems. — long prickles — base on young stems and adult stems: shape is narrow and oval, length is approximately 0.6 cm on average, and width is approximately 0.2 cm on average. — long prickles — color on young stems: commonly near Greyed-Yellow Group 161B at the base and near Yellow-Green Group 153D at the tip. — long prickles — color on adult stems: commonly near Greyed-Orange Group 165A. — small prickles — quantity: absent.
*Internode.*—Numbers on the entire branch: typically between 5 to 7. — length: typically between 3.0 cm to 6.0 cm on average.

Foliage:

*General appearance.*—Dense, with a semi-glossy aspect.
*Number of leaflets.*—3, 5, 7; most often 5.
*5 leaflets leaf.*—Length: typically between 7.5 cm to 10 cm. — width: typically 5.5 cm to 7.5 cm.
*Terminal leaflet.*—Length: typically between 3.0 cm to 4.5 cm. — width: typically between 1.8 cm to 2.5 cm.

*New foliage.*—Upper surface color commonly near Yellow-Green Group 144A. — under surface color commonly near Green Group 139C. — anthocyanin coloration: absent.

*Adult foliage.*—Upper surface color commonly near Green Group 137A. — under surface color commonly near Green Group 138B. — anthocyanin coloration: absent.

Leaflets:

*Shape.*—Top: acute. — base: cuneiform.

*Glossiness of upper surface.*—Medium.

*Texture.*—Upper surface is leathery and under surface is thick.

*Smoothness.*—Upper surface is smooth; under surface is bumpy.

*General appearance.*—Elliptical.

*Serration.*—Small and single.

*Undulation on the margin.*—Medium.

*Venation.*—Color is commonly near Green Group 137B and pattern is imparipinnate.

*Petiole rachis.*—Color of upper surface: commonly near Green Group 143C. — color of under surface: commonly near Yellow-Green Group 144B. — texture: upper surface is slightly glandular, under surface is smooth with very few prickles (2 to 5). — rachis of terminal leaflet: length is commonly between 2.5 cm to 3.5 cm and diameter is approximately 0.1 cm on average.

*Petioles.*—Upper surface: very few glandular. — under surface: no prickles. — color of upper surface: commonly near Green Group 137B. — color of under surface: commonly near Yellow-Green Group 146C. — length: typically between 1.8 cm to 2.3 cm on average. — diameter approximately 0.1 cm on average.

*Stipules.*—Length: typically between 0.9 cm to 1.2 cm on average. — width: approximately 0.1 cm on average. — general appearance: narrow. — texture: smooth. — color of upper surface: commonly near Green Group 139C. — color of under surface: commonly near Green Group 138C.

Inflorescence:

*Number of flowers per stem.*—10 per stem between 5 and 50 flowers per stem.

*Lastingness of the bloom.*—On the plant: approximately 2 weeks. — in vase: not tested.

*Bud.*—Shape: conical. — size: small. — length: approximately 1.2 cm on average. — width: approximately 0.9 cm on average. — color as calyx breaks: upper surface: commonly near Yellow Group 11B, basal spot is very little and near Yellow Group 7B. under surface: commonly near Yellow Group 11A, no basal spot.

*Sepals.*—Number commonly 5. — length: approximately 1.3 cm on average. — width: approximately 0.6 cm on average. — shape: at the top: elongated and narrow. at the base: flat at union with the receptacle. — extensions: very little extensions on 3 sepals; length is approximately 0.3 cm, and width is typically less than 0.1 cm. — upper surface: texture: tomentous. color commonly near Yellow-Green Group 146D. — under surface: texture: smooth. color commonly near Yellow-Green Group 147D.

*Receptacle.*—Color commonly near Yellow-Green Group 146D. — length: approximately 0.4 cm on average. — width: approximately 0.4 cm on average (on median part). — surface: tomentous. — shape: funnel shaped.

*Peduncle.*—Length: typically between 1.2 cm to 1.5 cm. — width: approximately 0.1 cm on average. — surface: glandular. — color commonly near Yellow-Green Group 146D.

*Flower.*—Diameter when open: approximately 4.0 cm on average. — depth of the flower approximately 2.5 cm on average. — shape: flat cup shaped. — shape when viewed from above: irregular rounded. — shape of the upper part of the flower profile: flat. — shape of the lower part of the flower profile: flattened convex. — type: double. — number of petals under normal conditions: typically 45 petals. — petals: shape: obovate (acute at the base and rounded at the top). texture: thick. length: typically 1.0 cm to 1.8 cm. width: typically 0.8 cm to 1.6 cm. — undulation of the petal: very weak. — reflexing of the petal: medium. — petal incision: very weak. — petal arrangement: imbricated with some petaloids (distorter not really fix shape). — petal drop: petals drop off cleanly before drying. — fragrance: slightly (sweet). — discoloration of the flower. Yes, to Green-White Group 157D. — color when opening: basal spot on the upper surface: commonly near Yellow Group 3B. upper surface: commonly near Yellow Group 11B on the center evolved to near Yellow Group 11D to the external of the flower. basal spot on the under surface: absent. under surface: commonly near Yellow Group 11B on the center evolved to near Yellow Group 11D to the external of the flower. — color of the open flower: basal spot on the upper surface: absent. upper surface of the flower commonly near Yellow Group 11D. basal spot on the under surface: absent. under surface of the flower commonly near Yellow Group 11D. — color of the flower when fading: same as the open flower. — anthers: number is 50 on average, length is approximately 0.15 cm on average, width is approximately 0.1 cm on average, coloration is commonly near Yellow-Orange Group 22A, and arrangement is regular around styles. — filaments: length is typically between 0.2 cm to 0.4 cm and coloration is commonly near Yellow-Orange Group 14A. — styles: length is approximately 0.4 cm on average, coloration is commonly near Greyed-Yellow Group 160A at the basal part and near Greyed-Purple Group 185A at the top, and number is approximately 25 on average. — stigmas: length is approximately 0.1 cm on average and coloration is commonly near Greyed-Orange Group 163B. — pollen: color is commonly near Greyed-Orange Group 163A and amount is very abundant. — hips: length is typically between 1.5 cm to 2.0 cm, width is approximately 1.3 cm on average, color is commonly near Yellow-Green Group 146C, and shape is egg shaped. — seed: not available at this stage; new variety does produce seeds.

Development:

*Vegetation.*—Strong.

*Blooming.*—Early in the season, abundant and recurrent, typically from May to November in France.

*USDA hardiness zone.*—Zone 4 to 11.

*Tolerance to disease.*—Good, and particularly against Black spot (*Diplocarpon rosae*).

The new 'MEIDEVI' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIDEVI' characterized by the following combination of characteristics:

(a) forms cream colored flowers, (b) produces double flowers, and (c) exhibits a ground cover habit;

substantially as herein shown and described.

* * * * *

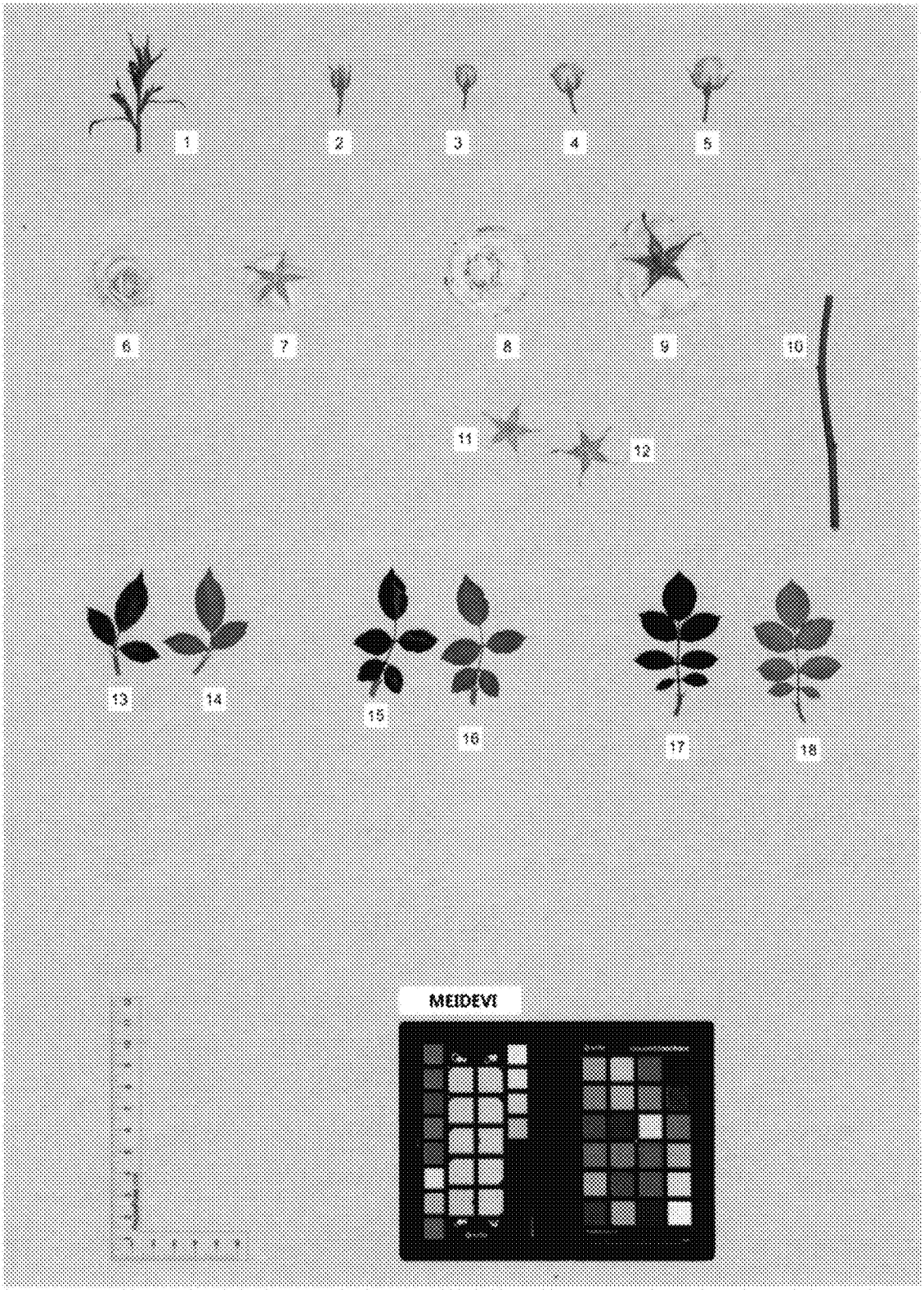
1
2
3
4
5
6
7
8
9
10
11
12
13
14
15
16
17
18
MEIDEVI